(12) United States Patent
Kickelhain et al.

(10) Patent No.: US 6,178,812 B1
(45) Date of Patent: Jan. 30, 2001

(54) METHODS FOR MEASURING THE SORBATE CONTENT OF SUBSTRATES

(75) Inventors: Joerg Kickelhain, Neustadt; Olaf Schulz, Berlin; Frank Imkenberg, Hannover, all of (DE)

(73) Assignee: LPKF Laser & Electronics AG, Garbsen (DE)

( * ) Notice: Under 35 U.S.C. 154(b), the term of this patent shall be extended for 0 days.

(21) Appl. No.: 09/367,263

(22) PCT Filed: Dec. 15, 1998

(86) PCT No.: PCT/DE98/03691

§ 371 Date: Aug. 13, 1999

§ 102(e) Date: Aug. 13, 1999

(87) PCT Pub. No.: WO99/31502

PCT Pub. Date: Jun. 24, 1999

(51) Int. Cl.[7] ................................................. G01N 50/04
(52) U.S. Cl. ................................ 73/73; 73/75; 73/865.6
(58) Field of Search .................................. 356/432, 436, 356/433, 440, 434; 73/76, 73, 25, 75, 865.6; 374/14, 28; 177/25.14

(56) References Cited

U.S. PATENT DOCUMENTS

| | | |
|---|---|---|
| 4,823,595 | 4/1989 | Hamed et al. . |
| 4,838,705 | 6/1989 | Byers et al. . |
| 4,934,181 | * 6/1990 | Gunderson ................................. 73/73 |
| 5,257,532 | * 11/1993 | Hayakawa et al. ....................... 73/75 |
| 5,685,192 | * 11/1997 | Shriner et al. ............................ 73/73 |

* cited by examiner

Primary Examiner—Hoa Q. Pham
(74) Attorney, Agent, or Firm—Evenson, McKeown, Edwards & Lenahan, P.L.L.C.

(57) ABSTRACT

The invention relates to methods for measuring the sorbate content in substrates, using a sensor with a measuring chamber. Said chamber contains a support medium whose partial pressure of sorbate is determined in order to determine the sorbate content of the substrate. According to the first method, the temperature of the support medium is varied up to a value at which the partial pressure of sorbate in the measuring chamber no longer varies with the temperature of the support medium, and slightly over this value. This partial pressure of sorbate is then used to determine the sorbate content of the substrate. According to the second method, the temperature of the support medium is kept essentially constant and the speed at which the partial pressure of sorbate of the support medium approaches the stable end value is determined. The sorbate content of the substrate is then determined taking into account the known dependency relationship between said speed and the vapor or solution partial pressure in the substrate. The two methods provide a way of measuring relatively high humidity contents of substrates based on the determination of the equilibrium moisture content.

19 Claims, 2 Drawing Sheets

METHODS FOR MEASURING THE SORBATE CONTENT OF SUBSTRATES

BACKGROUND OF THE INVENTION

The invention relates to a method for measuring sorbate contents in substrates, especially of moisture contents in compost, and also a sensor for the practice of the method.

Sorbates, i.e., absorbed substances, especially water, constitute an important factor in the processing, transportation and storage of substrates. Thus, through the adjustment of the moisture in the substrate, a great influence can often be exercised on weight, volume and possible ongoing biological processes. Therefore a precise determination of the moisture in a substrate as well as in the environment, for example, is of great importance.

Unlike the measurement of sorbates in the environment, there are only a relatively small number of measuring methods available for determining the sorbate content of solids.

The method of the gravimetric determination of the moisture content of a substrate is, for example, the basis of the apparatus and corresponding method described in DE 38 19 335 A1. In this method samples are taken and then dried and volatile components are driven from the sample with heat, and the water is collected and its mass is determined. This method has the disadvantage that it is not possible to use it to obtain information for a desired prospective conduct of a process, which is essential for the economical operation of technically complicated composting installations. Another disadvantage of the gravimetric measurement process is that it measures not only the moisture content of the substrate, caused by physiochemical or mechanical absorption or binding (see e.g., A. W. Lykow: "Experimentelle und theoretische Grundlagen der Trocknung," VEB Verlag Technik Berlin, p. 62–63), which is biologically relevant, but it also includes in the measurement the chemically bound water, which is very tightly bonded and therefore not biologically relevant.

The known moisture sensors prove to be too inaccurate and unusable.

In the foods industry a tensiometric measuring process is known in which a sensor containing a measuring chamber is introduced into the substrate on a measuring lance, for example (W. Lück: "Feuchtigkeit - Grundlagen, Messen, Regeln" , R. Oldenbourg, Munich, Vienna, 1964, pp. 179–182). In the measurement of moisture, on the basis of diffusion of water molecules, an equilibrium between the water vapor partial pressure of the substrate and the water vapor partial pressure of the air as carrier medium takes place in the measuring chamber. After a certain time, therefore, the moisture of the air in-the measuring chamber is constant. At this moisture—the so-called equilibrium moisture—the air in the measuring chamber is in equilibrium, i.e., just as many water molecules are leaving the substrate as are entering the substrate.

This equilibrium moisture constitutes a specific value of the relative air humidity (ratio of absolute to maximum air humidity) from which the moisture content of the substrate can be deduced if the temperature of the substrate is known.

This process based on using the properties of the equilibrium moisture exists in different embodiments, as for example using also a surface sensor for flat substances. Such a system is described in DE 36 34 518 A1 among others.

The known tensiometric process has the advantage over the gravimetric process that the chemically bound water does not enter into the measurement. Instead, only the moisture content of the substrate is measured, which is biologically relevant. A disadvantage of the method of measuring moisture by means of the equilibrium moisture is, however, that it can be used only on hygroscopically moist substances, but not on wet substances, since the air above the latter is saturated with water vapor (see W. Lück, loc. cit.). Thus the known method has heretofore been used only in areas in which relatively low moisture contents are to be determined or controlled. This measuring method can be applied in the case of garbage compost only when the moisture content of the substrate is only up to about 40%. In the case of biocompost, measurements are possible only up to about 10% moisture content of the substrate. The reason for this is that above this substrate moisture content the air in the measuring chamber is saturated, as a rule, i.e., the relative air moisture amounts to 100%. Since the air is saturated, however, no conclusion as to the moisture content of the substrate is possible. In composting biogenic wastes, however, a compost moisture range between 50 and 60% is interesting, since the microorganisms work best under these ambient conditions.

On the other hand, however, it is desirable to perform the measurement of the moisture content of the substrate by measuring the equilibrium moisture so as not to include the chemically bound water in the measurement.

SUMMARY OF THE INVENTION

The invention is therefore addressed to the problem of makiing a me thod available for measuring sorbate c ontents in substrates which is b ased on measuring the equilibrium moisture and will also permit measuring a relatively high sorbate content in the substrate, and also will make a sensor available for the practice of the method with which the effect of the measurement on the substrate will be slight.

This problem is solved with respect to the method by the method and apparatus of the invention.

The invention utilizes the physical principle that the ability of a medium to absorb a sorbate varies with the temperature. For example, the higher the temperature of the air is, the later it becomes saturated with water molecules. To show this, in FIG. 1 the maximum water vapor pressure of air is represented in relation to the temperature of the air.

In the method of the invention a sensor is used with a measuring chamber which contains a carrier medium whose sorbate partial pressure is determined, and from that the sorbate content of the substrate is obtained taking into consideration the measured, substantially constant temperature. Due to the fact that the temperature of the carrier medium is varied in the measuring chamber up to and slightly above the level at which the sorbate partial pressure in the measuring chamber no longer varies with the temperature of the carrier medium, it is brought about that a temperature is established at which the carrier medium in the measuring chamber is not saturated with sorbate molecules. Thus the sorbate content of the substrate can be determined from this sorbate partial pressure. For the sorbate partial pressure of the carrier medium, which is independent of the temperature of the carrier medium, is equal to the vapor or solution partial pressure of the sorbate in the substrate, depending on whether the substrate is surrounded by a gas or by a liquid. Taking into account the likewise measured temperature of the substrate it is possible to reckon the sorbate content from the vapor or solution partial pressure of the sorbate in the substrate.

The method of the invention has the advantage that relatively high sorbate contents, especially moisture contents, of substrates can be measured based on a determination of the thermodynamic state of equilibrium and thus, in the composting of biogenic wastes, they can be measured without including the biologically irrelevant water.

The method of the invention is thus advantageous especially in determining the relatively high moisture contents of composting plants. The influence of a warmer carrier medium on the substrate temperature in the measuring chamber is kept low by not keeping the carrier medium constantly at a high temperature level.

According to an advantageous embodiment of the invention, the temperature of the carrier medium in the measuring chamber is initially at a level at which the carrier medium is saturated with the sorbate. By a subsequent variation of the temperature of the carrier medium—as a rule an elevation of the temperature—the sorbate partial pressure of the carrier medium in the measuring chamber at first rises. At the same time the carrier medium continues to be saturated with sorbate until the temperature of the carrier medium is reached at which the saturation sorbate partial pressure of the carrier medium is equal to the vapor or solution partial pressure of the sorbate in the substrate. Upon a further elevation of the temperature the sorbate partial pressure of the carrier medium does not increase no further but remains constant. This constant sorbate partial pressure of the carrier medium is used for the above described determination of the moisture content of the substrate.

It is advantageous to vary the temperature of the carrier medium in the measuring chamber continuously, and determine the corresponding sorbate partial pressure of the carrier medium. Thus the sorbate partial pressure of the carrier medium can be recorded, for example.

The sorbate partial pressure of the carrier medium can be measured directly, but it can also be determined by a calibration curve recorded according to th temperature of the carrier medium.

The problem is furthermore solved by the method involving determining the speed at which the sorbate partial pressure approaches a stable end value. In this method of the invention a sensor with a measuring chamber is likewise used, which contains a carrier medium whose sorbate partial pressure is determined, from which the sorbate content of the substrate is determined in consideration of the substantially constant measured temperature of the sorbate. If the temperature of the carrier medium in the measuring chamber is substantially constant, the speed with which the sorbate partial pressure of the carrier medium approaches a stable end value is determined. Since this speed of approach depends upon the vapor or solvent pressure of the sorbate in the substrate, the vapor or solvent partial pressure of the sorbate in the substrate can be determined from the speed of approach. Taking into account the likewise measured temperature of the substrate, it is possible to determine the desired sorbate content of the substrate via the vapor or solvent partial pressure of the sorbate in the substrate.

This method also has the advantage that relatively high moisture contents of substrates can be measured based on a determination of equilibrium moisture.

In this method of the invention it is very advantageous toward its simplification if the surface of the substrate is made so large that it does not limit the speed of transport of the sorbate molecules into the measuring chamber and thus limit the speed of approach. Whether the surface of the substrate is sufficiently large can be determined based on measurements of the speed of approach for several temperature levels of the carrier medium. Even though this method can be used at a carrier medium temperature at which the carrier medium is saturated with sorbate at the stable end value, it is nevertheless advantageous to set the temperature of the carrier medium in the measuring chamber such that the carrier medium is not saturated at the stable end value.

According to an advantageous embodiment of the invention the sorbate partial pressure of the carrier medium is determined in both methods by measuring the absorption of laser light by the sorbate molecule. Advantages of the measurement, described in greater detail below, of the sorbate partial pressure by means of laser light lie in the accuracy and the speed of the measuring method.

Air is especially suitable as the carrier medium. However, other media are also possible, such as for example another gas, a liquid or a solid. The choice of a suitable carrier medium is made from the viewpoint of keeping a good ratio of the dependence on one another of the relative sorbate content in the carrier medium and the sorbate content in the substrate. This interdependence is called the "sorption isotherm."

A sensor is described hereinafter which can be used for the practice of the method of the invention. This sensor contains a measuring chamber whose temperature is controlled by a temperature controlling unit which is surrounded by a thermal insulation and is provided with openings in the form of bores which are small in proportion to the volume of the measuring chamber. For example, the ratio of the total cross-sectional area of all bores to the total area of the measuring chamber walls should not or not substantially exceed 15%. Furthermore, the sensor has at least one temperature sensor for measuring the temperature in the measuring chamber, at least one temperature sensor for measuring the temperature of the substrate, and a measuring device for determining the sorbate partial pressure. The thermal insulating layer can be, for example, a layer of air situated between an inner and an outer envelope of the measuring chamber. Also, provision can be made according to the invention for the volume of the measuring chamber to be kept as small as possible. By this configuration of the measuring chamber and the thermal insulation layer it is brought about that the temperature difference produced by the method between the carrier medium in the measuring chamber and the substrate constitutes only a negligibly small driving force for the establishment of a physical state of equilibrium. This is because the exchange of sorbate molecules of the carrier medium with the substrate is kept so low that the temperature of the substrate is but slightly affected and the stable state of the substrate can be sustained over a long period. In this manner the substrate is not detectably influenced by the measurement.

If the sensor is to be used exclusively for the practice of the method in which the speed at which the substrate partial pressure approaches a stable end value is determined, the temperature sensor for measuring the temperature in the measuring chamber is desirable but not essential.

As described above, it is advantageous if the sensor, if it contains a translucent carrier medium, has a laser measuring section with a laser to pass light through the measuring chamber, and a detector.

A control system is provided for controlling the sensor. It can be arranged so that it serves not only for supplying electricity to the sensor but also is designed using known means that it permits an automatic performance of the particular process.

BRIEF DESCRIPTION OF THE DRAWINGS

The method of the invention, and a sensor provided therefor according to the invention, are further explained

DETAILED DESCRIPTION OF THE PREFERRED EMBODIMENTS

Figure 1:
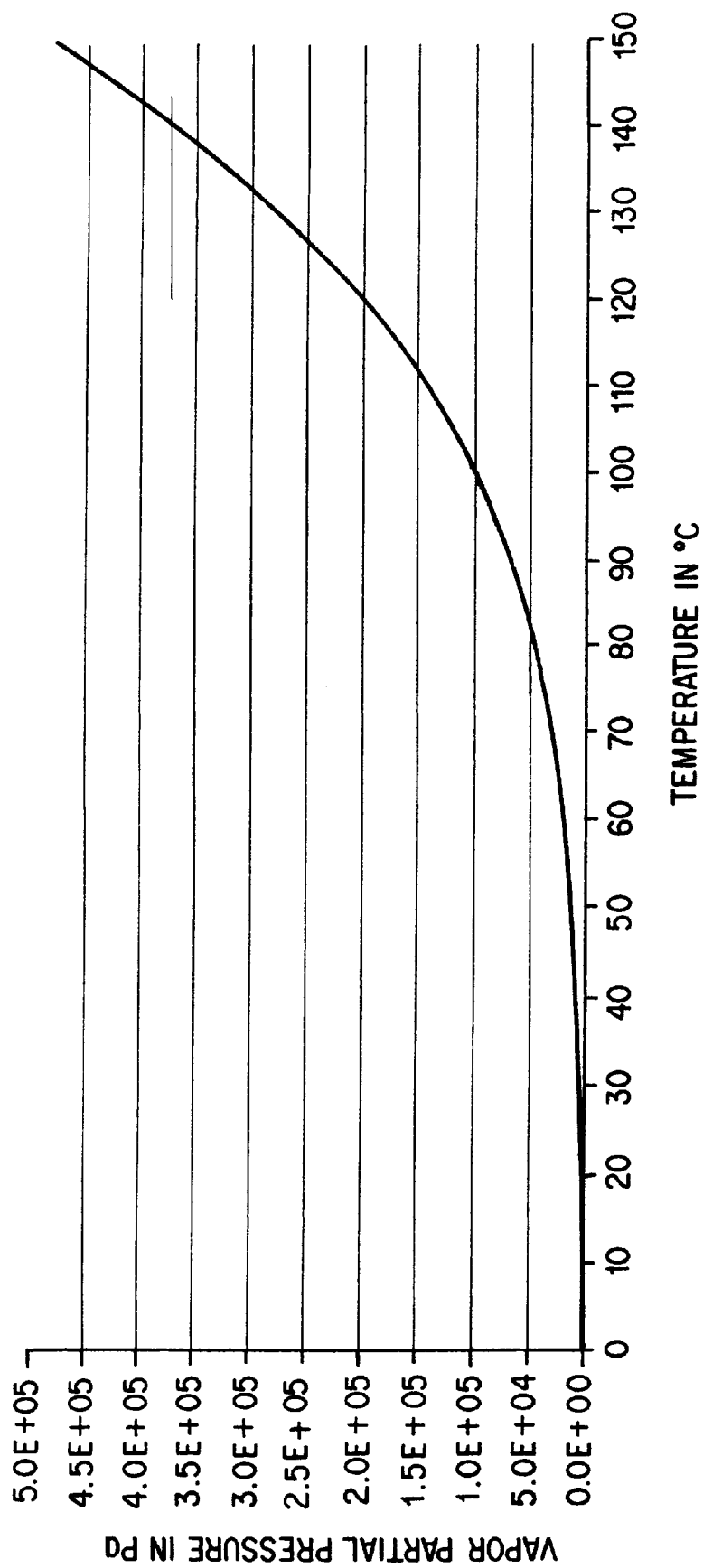
FIG. 1 shows the ability of air to absorb water molecules in relation to temperature.

In FIG. 1 the absorptivity of air for water in relation to temperature is represented, the water vapor pressure being recorded on the ordinate in Pascals (Pa). The maximum water vapor pressure increases progressively with increasing temperature, with the result that the greater the temperature of the air is, the later the air becomes saturated with water molecules.

This property is exploited in the embodiment of the method in which the measuring chamber is heated until the sorbate partial pressure no longer increases, which is now to be described. At first a relatively low temperature is established in the carrier medium in the measuring chamber. Then the sensor is brought into contact with the substrate being measured, so that an exchange can take place between sorbate molecules of the substrate—water molecules in this case—and those of the carrier medium. Since initially the water vapor partial pressure of the substrate is greater than the water vapor partial pressure of the carrier medium, at first a directional transport of water molecules into the carrier medium takes place on account of a spatial concentration gradient of water molecules. Equilibrium is complete when either the water vapor partial pressures of the substrate and of the carrier mediuni are equal or the carrier medium is saturated, i.e., the carrier medium has reached a relative humidity of 100%. Then the same number of water molecules diffuse in both directions, namely out of the carrier medium and into the carrier medium.

Figure 2:
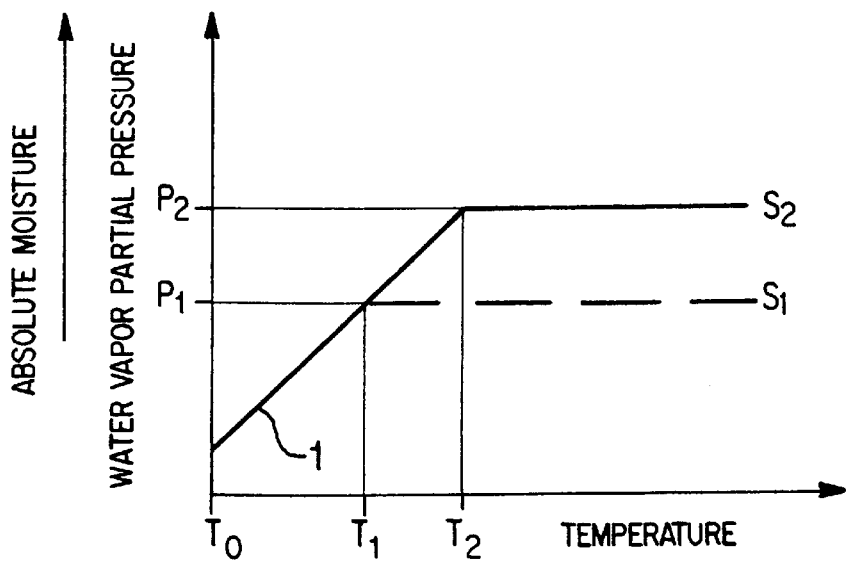
FIG. 2 shows the absorption of sorbate in the measuring chamber in relation to the temperature of the carrier medium in the measuring chamber.

In the present example the temperature of the carrier medium $T_0$ in the measuring chamber is set so low that the carrier medium is saturated. Then the temperature of the carrier medium in the measuring chamber is increased, while an additional transfer of water molecules from the substrate to the support material takes place. At the same time the carrier medium continues to be saturated. The corresponding section of the c;urve of the water vapor partial pressure in the carrier medium is indicated at 1 in FIG. 2. The curve section 1 of the water vapor partial pressure is linear and is always at 100% relative humidity of the carrier medium. The curve of this water vapor partial pressure does not change until the temperature of the carrier medium is reached at which the saturation vapor pressure is equal to the water vapor partial pressure of the substrate. This temperature is indicated in FIG. 2 at $T_1$. As the temperature of the carrier medium rises further in the measuring chamber the water vapor partial pressure of the carrier medium remains constant, and it is below the saturation water vapor partial pressure of the carrier medium. Thus, the curve of the water vapor partial pressure of the carrier medium marked $S_1$, is obtained for the substrate.

The value of the water vapor partial pressure of the carrier medium, marked $p_1$, is equal to the water vapor partial pressure of the substrate. The water vapor partial pressure of the substrate is proportional to the absolute moisture content of the substrate. Since the proportionality factor is known, the targeted absolute moisture content of the substrate can be determined from the water vapor partial pressure $p_1$. The chemically bound water is ignored, since on account of the bond it does not contribute to the water vapor partial pressure ofthe substrate.

In FIG. 2 an additional curve $S_2$ of the water vapor partial pressure of the carrier medium is shown, which was measured on the same substrate, but one containing a different moisture content. This substrate has a higher water vapor partial pressure than the first substrate, so that the carrier medium comes out of the saturation range only at a higher temperature, namely the temperature $T_2$. Thus for this substrate the water vapor partial pressure $p_2$ is measured.

In this method the temperature of the air in the measuring chamber, namely that of the carrier medium, must be raised until the water vapor partial pressure no longer increases, so that the carrier medium is no longer saturated. At the same time a stable water vapor partial pressure is obtained as an excellent value of the water vapor partial pressure beyond a certain temperature. Whereas when the carrier medium is saturated no conclusion as to the water vapor partial pressure of the substrate is possible, the stable value of the water vapor partial pressure of the carrier medium is equal to the water vapor partial pressure of the substrate and can thus be used to determine the absolute moisture content.

Figure 3:
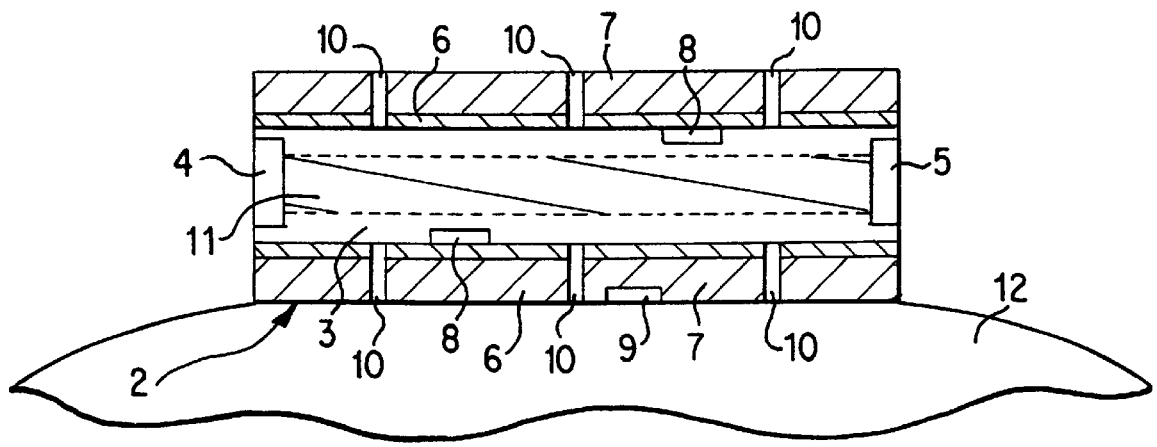
FIG. 3 shows a schematic drawing of one design of a sensor according to the invention.

The sensor 2 according to the invention, shown in FIG. 3, has a measuring chamber 3 which contains a carrier medium (not shown). The measuring chamber 3 is surrounded by a heat-conducting material. At one end of the measuring chamber 3 a laser source 4 with focusing means (not shown) is mounted. At the opposite end of the measuring chamber 3 is a detector 5 which likewise has a focusing means (not shown). The measuring chamber 3 is substantially defined in the longitudinal direction by temperature controlling elements 6 in the form of heating wires. These temperature controlling elements 6, however, can also be Peltier-effect elements. Between the temperature controlling elements 6 and the outer wall of the sensor 2 are thermal insulating layers 7 which are formed by sealed chambers filled with air. Two temperature sensors 8 in the form of platinum resistors are mounted on the temperature controlling elements 6 within the measuring chamber 3. Another temperature sensor 9 is provided within one of the thermal insulating layers 7 on the outside wall of the sensor 2. On each longitudinal side of the sensor 2 are three bores 10 which pass through the thermal insulating layer 7 and the temperature controlling element 6. The bores 10 permit an exchange of the sorbate, but are impermeable to the substrate.

The laser source 4 and the detector 5 constitute a laser measuring system 11. By the temperature controlling element 6 and the temperature sensors 8 the temperature of the carrier medium in the measuring chamber 3 is adjusted by means of a control device not shown.

With the temperature sensor 9, which is in contact with the substrate 12, the temperature of the substrate can be measured. The thermal insulation layers 7 are intended to minimize the transfer of heat from the measuring chamber 3 and temperature control elements to the substrate. Since the measuring chamber is surrounded by heat-conducting material a uniform temperature is created in the measuring chamber 3 in a minimum of time. The bores 10 are diffusion passages for the exchange between the carrier medium and the transport medium surrounding the substrate and carrying the sorbate molecules into the measuring chamber 3. The bores 10 have a small diameter in comparison to the length of the measuring chamber 3. By means of the laser measuring system 1 it is possible to determine the sorbate content in the carrier medium by absorption spectroscopy wherein the carrier medium is penetrated by a first laser beam of the wavelength of an absorption maximum of the water molecules contained in the carrier medium and the unabsorbed laser radiation is measured with a detector. Additionally, a second laser beam is used which has a wavelength that is not absorbed by the water molecules. This laser radiation is also measured with a detector. The readings are recorded and the water content of the carrier medium is calculated from the difference between them.

The sensor can be put into the substrate by means of a measuring lance and thus can be used at any point in the substrate to measure the sorbate content. Likewise, an embodiment of the measuring lance can contain several of these sensors and thus permit the measurement of the sorbate in several planes of the substrate with only one measuring lance.

Furthermore, the method of the invention in which the spped at which the sorbate partial pressure approaches a stable end value is determined will now be explained with reference to an embodiment in which the moisture content of a substrate is likewise to be measured.

The sensor 2 described above is used, and air is again chosen as the carrier medium. The temperature of the carrier medium in the measuring chamber is adjusted so that no saturation of the carrier medium in the measuring chamber is to be expected at the moment in which the stable end value of the water vapor partial pressure of the carrier medium is reached.

The sensor 2 is introduced into the substrate. Since in the substrate the water vapor partial pressure is higher than it is in the carrier medium, here again a directional transport of water molecules into the measuring chamber 3 takes place. At the same time the speed at which the water vapor partial pressure of the carrier medium approaches the stable end value, and thus the speed of the equalization of the water vapor partial pressure in the substrate and in the carrier medium is dependent upon the magnitude of the difference between the water vapor partial pressure in the substrate and in the carrier medium. The equalization takes place for as long as no pressure difference exists, provided that no saturation of the carrier medium with water occurs in the measuring chamber. Otherwise no further pressure equalization takes place.

During the equalization, the water vapor partial pressure is constantly recorded by the laser measuring system in relation to the measured time. The speed of approach results from the first derivation of the change in the water vapor partial pressure of the carrier medium over time, which thus corresponds graphically to the rise of the recorded measuring curve. Thus it is possible to derive the moisture content in the substrate from the measurement of at least two values of the water vapor partial pressure of the carrier medium, observing the time difference between the values measured during the equalization process.

It can generally occur in the practice of the method that the speed of approach is limited by marginal conditions, so that it does not reach its possible maximum value. Limiting conditions can be a small surface area of the substrate or also a low molecule mobility of the sorbate in the carrier medium. Basically, therefore, great care should be taken to see that the surface area of the substrate is so great that it does not limit the speed of approach to the stable end value of the partial pressure of the sorbate in the supporting medium.

It is not easily possible to estimate these marginal conditions in the operation. If the temperature of the carrier medium is adjusted to a value such that no saturation of the carrier medium in the measuring chamber takes place during the equalization process, all phases of the equalization are recorded and it becomes possible to investigate the equalization process for limiting marginal conditions. When the sorbate partial pressure difference is very slight, the speed of approach is very low, and then it is possible to assume an unlimited equalization. The calibration of the measurements of the sorbate partial pressure in the measuring chamber 3 is performed through the sorption isotherms as in the method in which the measuring chamber is heated until the sorbate partial pressure no longer increases.

Although the invention has been explained in connection with the measurement of water as the sorbate, it is to be understood, however, that sorbates other than water can also be measured in the scope of the invention.

What is claimed is:

1. A method for measuring the sorbate content of a substrate containing a sorbed material, said method comprising the acts of:

disposing a measuring chamber containing a carrier medium in communication with the substrate so that sorbate molecules can migrate from the substrate into the measuring chamber until the carrier medium is saturated with the sorbate;

while maintaining the substrate at a substantially constant temperature, heating the carrier medium in the measuring chamber so that the partial pressure of the sorbate increases therein;

sensing the partial pressure of sorbate molecules in the carrier medium in the measuring chamber and monitoring increases in the partial pressure of the sorbate in the measuring chamber until the partial pressure of the sorbate in the carrier medium in the measuring chamber equals the partial pressure of the sorbate in the substrate and further increases cease; and determining the sorbate content of the substrate from the maximum partial pressure of the sorbate sensed in the measuring chamber.

2. A method according to claim 1, wherein said substrate is composting vegetation and said sorbate is water.

3. A method according to claim 1, wherein the temperature of the carrier medium in the measuring chamber is increased, starting from a value at which the carrier medium is saturated with the sorbate.

4. A method according to claim 1, wherein the temperature of the carrier medium in the measuring chamber is continuously varied, and the sorbate partial pressure of the carrier medium is continuously determined.

5. A method according to claim 1, wherein the sorbate partial pressure of the carrier medium is measured directly.

6. A method according to claim 1, wherein the sorbate partial pressure of the carrier medium is determined from the carrier medium temperature by reference to a calibration curve of sorbate partial pressure verses carrier medium temperature.

7. A method according to claim 1, wherein the sorbate partial pressure of the carrier medium is determined by means of a measurement of the absorption of laser light by the sorbate molecules.

8. A method according to claim 1, wherein said carrier medium is air.

9. A method for measuring the sorbate content of a substrate containing a sorbed material, said method comprising the acts of:

disposing a measuring chamber containing a carrier medium in communication with the substrate so that sorbate molecules can migrate from the substrate into the measuring chamber;

sensing the partial pressure of sorbate molecules in the carrier medium in the measuring chamber and detecting the rate at which the partial pressure of the sorbate in the carrier medium approaches a stable end value;

determining the partial pressure of the sorbate in the substrate from the rate at which the partial pressure of the sorbate in the carrier medium approaches a stable end value; and determining the sorbate content of the substrate from the partial pressure of the sorbate in the substrate.

10. A method according to claim 9, wherein said substrate is composting vegetation and said sorbate is water.

11. A method according to claim 9, wherein the surface of the substrate in communication with the measuring chamber is of a sufficiently large size that the rate at which the partial pressure of the sorbate in the carrier medium approaches a stable end value is not limited by the size of said surface.

12. A method according to claim 9, wherein the temperature of the carrier medium in the measuring chamber is adjusted so that it is not saturated at the stable end value.

13. A method according to claim 9, wherein the sorbate partial pressure of the carrier medium is determined by means of a measurement of the absorption of laser light by the sorbate molecules.

14. A method according to claim 9, wherein said carrier medium is air.

15. A sensor for measuring the sorbate content of an adjacently disposed substrate containing a sorbed material, said sensor comprising:

a measuring chamber surrounded by a thermal insulating layer, said measuring chamber having at least one opening into said chamber through which sorbate molecules from the adjacently disposed substrate can migrate into the chamber;

a temperature control unit for controlling the temperature in the measuring chamber;

a substrate temperature sensor for sensing the temperature of the adjacently disposed substrate, and a measuring device for measuring the partial pressure of the sorbate in the measuring chamber.

16. A sensor according to claim 15, further comprising a measuring chamber temperature sensor for sensing the temperature in said measuring chamber.

17. A sensor according to claim 15, wherein said at least one opening has a size which is sufficiently small to prevent the adjacent substrate from entering the measuring chamber while permitting sorbate molecules from the substrate to diffuse into the measuring chamber until an equilibrium is reached.

18. A sensor according to claim 15, wherein said measuring device comprises a laser source arranged to emit a laser beam through said measuring chamber, and a detector arranged on an opposite side of said measuring chamber from said laser source for detecting laser light transmitted through said measuring chamber, whereby absorption of laser light by sorbate molecules in the measuring chamber can be measured and the partial pressure of sorbate in the measuring chamber can be determined.

19. A sensor according to claim 15, wherein said temperature control unit comprises heating elements for heating a carrier medium inside said measuring chamber.

* * * * *